United States Patent [19]
Lightner

[11] 3,988,921
[45] Nov. 2, 1976

[54] METHOD AND APPARATUS FOR SPOTTING CHROMATOGRAPHIC ELEMENTS

[76] Inventor: Gene E. Lightner, R.D. No. 1, Kennett Square, Pa. 19348

[22] Filed: Feb. 8, 1974

[21] Appl. No.: 440,807

[52] U.S. Cl. ............................. 73/61.1 C; 73/425.6
[51] Int. Cl.² ......................................... B01D 15/08
[58] Field of Search ....................... 73/61.1 C, 425.6

[56] References Cited
UNITED STATES PATENTS

| | | | |
|---|---|---|---|
| 3,189,413 | 6/1965 | Davis | 73/61.1 C |
| 3,193,358 | 7/1965 | Baruch | 73/423 A |
| 3,495,446 | 2/1970 | Williamson | 73/61.1 C |
| 3,843,323 | 10/1974 | Quame | 23/253 |

*Primary Examiner*—S. Clement Swisher
*Attorney, Agent, or Firm*—C. W. Mortenson

[57] ABSTRACT

According to the method disclosed, a capillary tube is first dipped into a sample receptacle and filled through capillary action. The tube is then withdrawn from the receptacle and lowered over a chromatographic plate such that the lower end of tube either just touches the plate or is spaced therefrom such that there is a small gap between the end of the tube and the plate. Air pressure is then applied to the other end of the capillary tube — in the first instance to drive the liquid in the capillary out onto the plate at a known rate; in the second instance air pressure is applied to the other end of the capillary tube to form a droplet that bridges the gap between the tube end and the plate. Once the droplet makes contact with the plate, it is sucked into the interstices of the coating material of the plate. In alternative methods of the invention, air pressure is used to control the volume of the sample admitted to the capillary tube. A resilient, closed container, such as a bellows, is used for this purpose. This same container is positioned to be compressed as the tube is lowered for spotting to aid in forming the droplet and/or exhausting the tube at a reproducible rate.

An apparatus is also disclosed for performing the method of this invention. This apparatus includes a capillary tube and a drive means for raising and then lowering the filled tube with respect to the chromatographic plate for spotting the plate, then rotating the tube to a filling position having a sample receptacle and lowering the tube into and out of the receptacle whereby the tube is filled by capillary action. The drive means may either maintain a predetermined gap between the lower end of the tube and the chromatographic element or allow the tube to touch the plate. An adjustable pressure means supplies a fluid pressure to the other end of the tube.

12 Claims, 3 Drawing Figures

METHOD AND APPARATUS FOR SPOTTING CHROMATOGRAPHIC ELEMENTS

BACKGROUND OF THE INVENTION

This invention relates to a method and apparatus for spotting chromatographic elements with a sample in a reproducible manner.

There is described in a patent application entitled "Automatic Thin Layer Chromatographic Apparatus" filed Jan. 11, 1973, Ser. No. 322,869 by Gene E. Lightner an apparatus for sequentially withdrawing an aliquot of a sample fluid to be analyzed from a supply magazine and transferring such sample aliquot to a chromatographic plate. The automatic apparatus described utilizes two pivotable arms, one a spotter arm, the second pick-up arm. The pick-up arm operates to pick-up chromatographic plates from a supply magazine and place them in a position for spotting. After being spotted with an aliquot of a sample fluid to be analyzed, the plates are transferred by the pick-up arm into discrete vertically disposed tanks positioned about a turntable. Solvent is applied to each tank immediately prior to insertion of the spotted plate therein. Upon development of a plate by the solvent, usually one complete rotation of the tank turntable, and after the solvent is drained from the tank, the pick-up arm picks up the developed plate and passes it down a chute to an automatic reader. The spotter arm has a capillary tube mounted on its end portions. This tube is dipped into the sample vials, which are disposed about a sample turntable in a ring-like fashion, and transfers a sample aliquot to a precise position on the lower edge of a chromatographic plate. A reference sample aliquot may be placed directly over the spot to provide an internal standard.

As is described in the said Lightner application, the capillary tube used for spotting is acutally brought into contact with the plate and raised and lowered several times to insure that all of the sample contained in the tube is transferred to the plate. The capillary action of the interstitial structure of the plate's coating is used to suck the sample from the capillary tube. While satisfactory, it has been found that in some instances acutal contact with the plate tends to disturb the coating material. This can in some cases effect the reeproducibility of the sample. In some cases the spot is sometimes caused to spread unnecessarily in the spotting region.

An even greater problem is the lack of reproducibility with all plate coatings. Some coatings do not provide a reproducible capillary flow rate. The quantity of fluid remaining on the inner walls of the tube will vary according to the flow rate at which the tube is exhausted, the solvents used and the characteristics of the particular capillary tube. Thus with varying flow rates caused by vagaries of the coatings, the liquid remaining on the capillary walls of the tube can and does vary from sample to sample and plate to plate. Naturally, this affects the reproducibility of the analysis.

Accordingly, it is an object of this invention to obviate many of the disadvantages incumbent in spottiing procedures often used in the prior art.

Another object of this invention is to provide an improved apparatus for reproducibly spotting chromatographic plates.

A further object of this invention is to provide an improved apparatus for spotting plates utilizing capillary tubes with positive pressure being used to control sample volume and, if desired, discharge rate of the sample fluid.

Another object of this invention is to provide an improved method of reproducibly spotting chromatographic plates.

BRIEF DESCRIPTION OF THE INVENTION

In accordance with this invention a method for reproducibly depositing a predetermined quantity of a liquid sample on a chromatographic element includes the steps of dipping one end of a capillary tube into the same thereby to at least partly fill the tube, positioning such end of the capillary tube contiguous to the chromatographic element, and applying a fluid pressure to the other end of the capillary tube, thereby to at least initiate the discharge of the liquid sample therefrom. Preferably, the fluid pressure is such as to maintain a constant, reproducible rate of liquid flow out of the capillary tube. Alternatively, both fluid pressure and capillary action of the chromatographic element are used to empty the capillary tube. Also, one end of the tube may be positioned such that there is a small gap between the tube and the element and the fluid pressure may be used simply to form a droplet at the one end of the tube of sufficient volume to bridge the gap between the end of the tube and the chromatographic element.

According to still other alternative methods of the invention, the fluid pressure at the other end of the capillary tube is adjusted to control the volume of the sample collected in the tube by capillary action. A resilient container may be coupled to the other end of the capillary tube such that the volume of the sample collected in the tube is controlled by the back pressure of the container opposing the capillary action in the tube. Also, the volume in the container may be decreased as a function of the proximity of the end of the tube to the chromatographic element, thereby to aid in forming the droplet or exhausting the tube.

A preferred apparatus for performing the method of this invention includes a capillary tube, a sample receptacle, a first drive means for raising and lowering one end of the tube with respect to the element and with respect to the receptacle, and a pressure means for applying a fluid pressure greater than the local atmospheric pressure to the other end of the tube, thereby to at least initiate the discharge of the sample fluid from said capillary tube. Alternatively, the fluid pressure may be used to drive the fluid from the tube at a controlled rate. In this manner liquid remaining on the capillary's walls will be the same with each sample and hence the samples are reproducibly spotted.

According to a preferred embodiment, the control means is responsive to the tube being lowered into the sample receptacle for adjusting the back gas pressure within the tube, thereby to control the volume of sample withdrawn into the tube. Alternatively, a resilient closed container may be connected by a conduit to the other end of the tube thereby to control the volume of filling of the tube by the back pressure of the container.

BRIEF DESCRIPTION OF THE DRAWINGS

The novel features that are considered characteristic of this invention are set forth with particularity in the appended claims. The invention, itself, however, both as to its organization and method of operation, as well as additioinal objects and advantages thereof, will be best understood from the following description when read in connection with the accompanying drawings, in which:

DETAILED DESCRIPTION OF THE PREFERRED EMBODIMENTS

Figure 2:
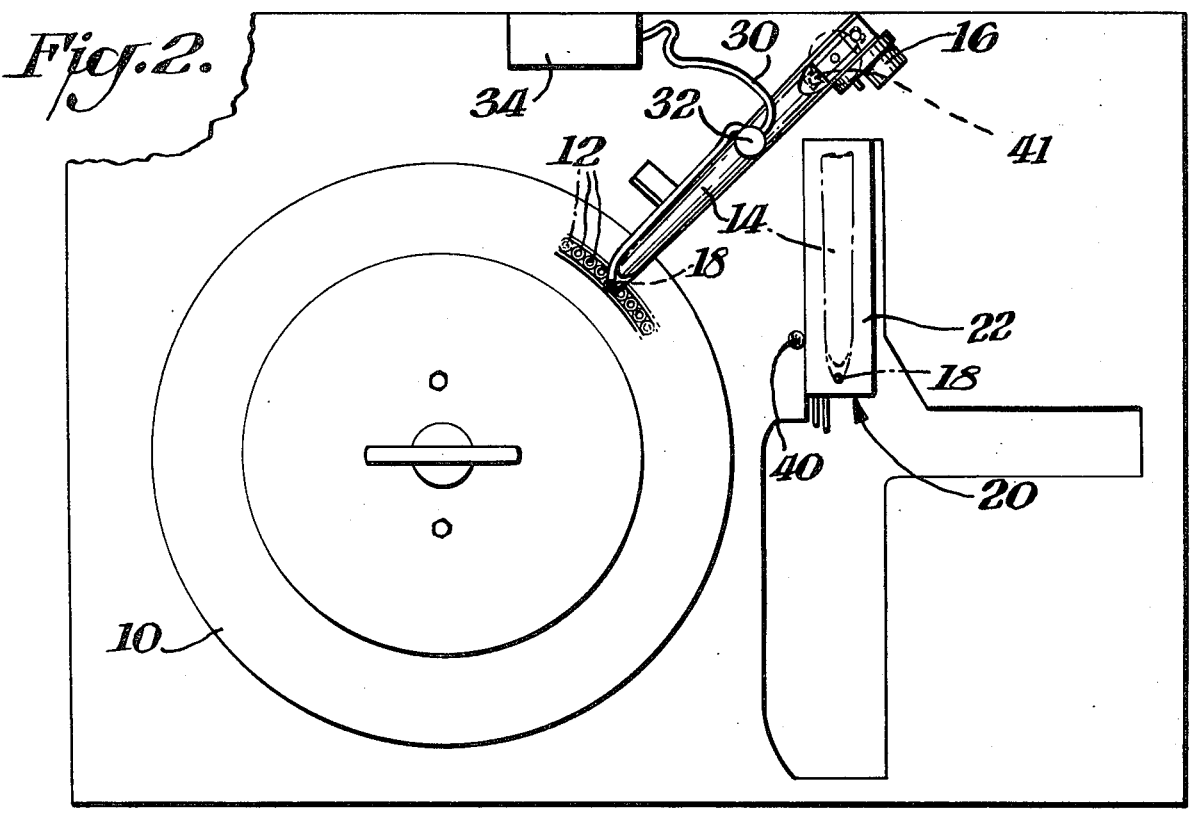
FIG. 2 is a plan view of the spotting apparatus illustrated in FIG. 1.
Figure 1:
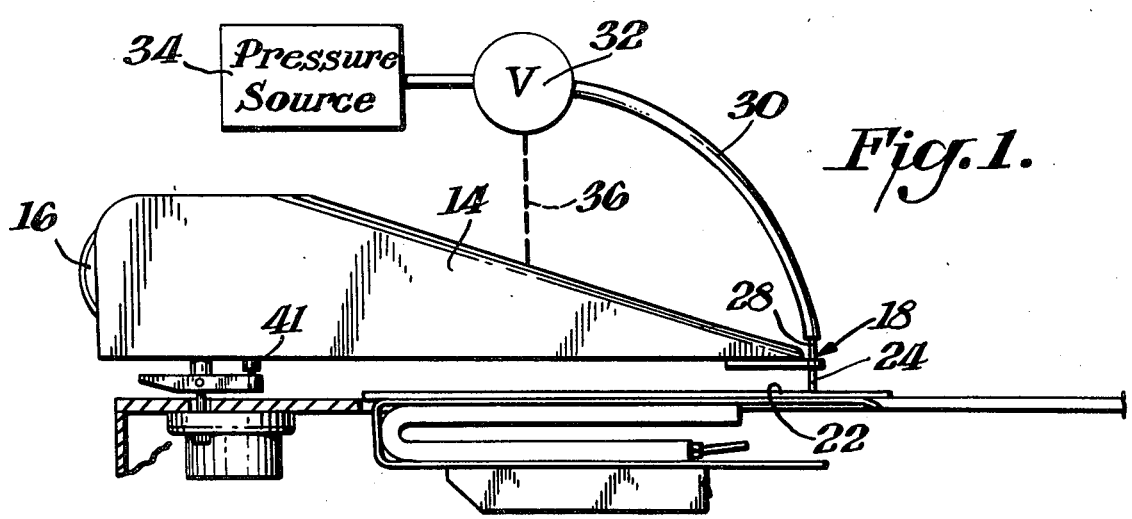
FIG. 1 is a side elevation view, partially in block form, of an automatic chromatographic plate spotting apparatus constructed in accordance with a preferred embodiment of this invention.

There is seen in FIGS. 1 and 2 a portion of an automatic thin layer chromatographic spotting and developing system such as that described in said Lightner application. Such system includes a turntable 10 having a plurality of sample vials 12 disposed in its periphery. The turntable rotates in increments such that each vial 12 is successively brought into a sample pick-up position. A spotter arm 14 driven by a suitable servodrive 16 pivots one end of the spotter arm. The remote end of the spotter arm 14 has secured thereto a capillary tube 18. The tube is positioned in a vertical manner such that when it is lowered by the spotter arm 14 its lower end is dipped into a sample vial 12 and withdraws a discrete sample aliquot by the capillary action of the tube. The tube 18 is then raised with the sample contained therein and the spotter arm 14 rotated counterclockwise over to a spotting position 20. At this point, a thin layer chromatographic element or plate 22 of known type is disposed in a horizontal plane. Unspotted plates are successively fed to the spotting position 20 to be spotted by a servo-transfer mechanism (not shown) such as that described in said Lightner application or by any suitable mechanism of known type. Thereafter, they are successively fed to a developing tank (not shown) by similar or the same transfer mechanism. As described by Lightner, the transfer mechanism maay use a vacuum pick-up for lifting and handling the plates.

The servo-drive 16 and spotter arm 14 lower the tubes to a point such that the lower end of the tube 24 extends to a point contiguous the plate 22. The point may be adjusted either by adjusting the servo system or by the use of a stop block such that the lower end of the tube lightly contacts the plate. Alternatively, the point may be just above, but not touching, the plate 22 in such a manner that there is a small gap therebetween. The gap is of the magnitude of a small droplet 26 (FIG. 3) that may be formed on the lower end of the tube 18 as will be described. In this manner, the droplet 26 of the sample fluid bridges the gap between the tube end and the plate 22. Since the thin layer plates are normally coated with a material which has a plurality of interstices formed therein, these interstices act as myriad individual capillary elements which exert a strong capillary attraction to the fluid of the droplet thereby sucking the entire droplet and the contents of the capillary tube out and onto the plate. By not actually contacting the plate, this spotting technique permits the reproducible spots to be formed on a plurality of plates. The spot, being applied in the same manner in each instance does not spread unnecessarily and furthermore, the surface of the plate is not destroyed or altered in any way by contact by the end of the capillary tube.

According to one method of this invention, the droplet 26 is formed on the end of the capillary tube by applying a slight positive pressure to the other end 28 of the capillary tube. This is accomplished in the preferred apparatus of the invention by connecting a resilient or flexible conduit 30 through a valve 32 to an adjustable fluid pressure souce 34. This fluid may be air or any other suitable gas, preferably an inert gas which is relatively insoluble in the sample fluid. The pressures required, of course, are very slight being only enough to exceed the capillary forces of the capillary tube. The valve 32 is controlled by a mechanical or electronic linkage depicted by the dashed line 36 such that as the tube 18 is lowered into the spotting position, the valve 32 is opened to apply a slight positive pressure sufficient to overcome the capillary attraction of the fluid and expel the fluid from the end of the tube sufficiently to form the small droplet 26 thereon. The magnitude of this pressure, of course, will vary with the density and to some extent the viscosity of the sample fluid and its surface attraction to the capillary tube itself. Preferably, the droplet may be only half formed permitting the capillary attraction of the interstices of the thin layer chromatographic plate to withdraw the fluid from the tube.

The valve linkage 36 operates to close the valve 32 during the time the sample is being withdrawn from the sample vials. In this manner, the back pressure within the flexible conduit 30 acts as a back pressure opposing the capillary action of the tube in withdrawing the sample fluid thereby controlling the volume of the sample withdrawn. In othe embodiments of the invention an alternate pressure source (not shown) may be connected to the valve 32 such that it may be introduced into the system for a more precise control of the filling operation. It has been found that the capillary attraction of the plate is usually quite sufficient to withdraw all of the sample from the capillary tube. The linkage 36 may be simply a mechanical finger sensor, a microswitch positioned to close as the spotter arm is lowered and thereby complete an electrical circuit to a solenoid which operates the valve, a photocell position sensor, or any other suitable sensor.

In many cases the individual plates 22 do not exhibit the same capillary attraction to the fluid sample. This would result in differing flow rates as the capillary tube is exhausted. As noted previously, the amount of fluid remaining on the walls of the capillary is a function of this discharge flow rate. Thus, to have the fluid amounts remain constant, the flow rates must be constant. Accordingly, in these cases, the pressure of the pressure souce may be increased to effect and control the rate at which liquid is driven from the sample tube. In other cases the pressure may be adjusted such that it only initiates the capillary flow from the tube 18. In either of these cases the tube positioning may be varied such that the tube actually contacts the chromatographic coating on the plate 22. This adjustment is accomplished either by the servo system alone or by the use of the stop member 41 to limit the downward movement of the arm 14 and, of course, a guide member 40 as described by Lightner. The guide member 40 provides a cam-like surface to position the tube relative to the plate.

Figure 3:
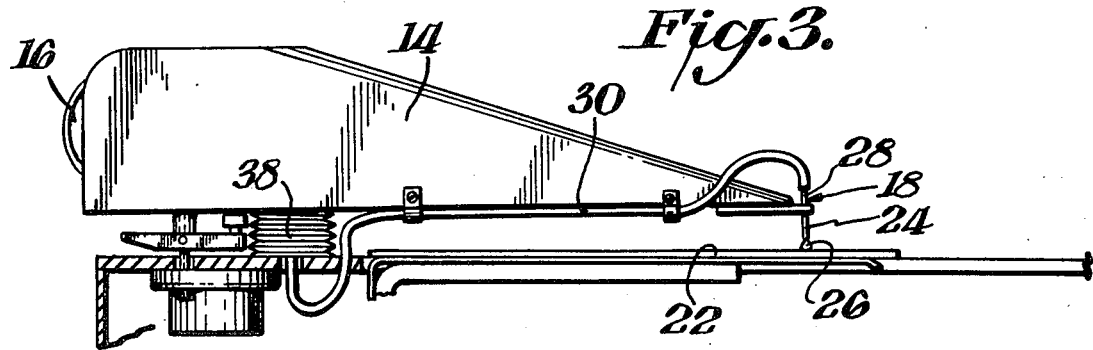
FIG. 3 is a side elevation view of an alternative apparatus utilizing a bellows which may be used in performing the method of this invention.

In another alternative embodiment of this invention illustrated in FIG. 3, a bellows 38 is connected to the spotter arm 14 and the conduit 30 is connected to the bellows. The bellows 38, formed of any suitable material such as rubber, may be resilient, or flexible, as the case may be, and is a closed airtight system. It is adjustably attached to the spotter arm 14 such that as the spotter arm is lowered into the position, the bellows 38 is slightly squeezed or compressed thereby applying a slight positive pressure sufficient to form the droplet on the lower end of the tube 18 as described previously. By positioning the bellows to be squeezed harder as the spotter arm is lower, the capillary tube may be exhausted by the resulting increase in air pressure. In like manner, when the spotter arm and capillary tube 18 are lowered into the sample vial, the back pressure of the bellows will resist or oppose the capillary action of the tube in withdrawing the sample. Depending upon the volume of the bellows and its resiliency, the bellows back pressure controls the volume of the sample in a highly reproducible manner. The bellows is filled preferably with air since it is an open system although any of the gases previously described may be used.

There has thus been described a highly precise, reproducible method of spotting chromatographic plates. this method may either contact or not the surface of the thin layer chromatographic plates and hence may avoid inflicting damage thereto. One method of the embodiment disclosed utilizes a slight positive pressure to aid in discharging the sample from the capillary tube without benefit of the capillary attraction of the plates interstitial structure. This permits the spotting of the plate to take place with one spotting motion which saves time and permits reproducible spotting to be effected.

According to the preferred apparatus of this invention, the upper end of the capillary tube is connected through a flexible conduit to a pressure source to control the formation of a droplet, to control the volume of sample withdrawn into the capillayr tube, and to effect the emptying of the tube in a reproducible manner. The pressure souce may be a bellows in one embodiment.

It is obvious that many embodiments may be made of this inventive concept, and that many modifications may be made in the embodiments hereinbefore described. Therefore, it is to be understood that all descriptive material herein is to be interpreted merely as illustrative, exemplary, and not in a limited sense. It is intended that various modifications which might readily suggest themselves to those skilled in the art by covered by the following claiams as far as the prior art permits.

What is claimed is:

1. A method of using a capillary tube for reproducibly depositing a predetermined quantity of a liquid sample on a chormatographic element comprising the steps of:
  A. dipping one end of said capillary tube into a first sample, and controlling the pressure to draw a controlled volume of said sample into said tube by coupling a closed resilient container to said other end of said capillary tube thereby to control the volume of said sample volume,
  B. positioning said end of said capillary tube contiguous said chromatographic element,
  C. applying fluid pressure to the other end of said capillary tube, thereby to deposit said liquid sample on said element in a controlled volume, and
  D. repeating steps (A), (B), and (C) in said controlled manner to discharge from said tube and to deposit on a second element a predetermined quantity of a second liquid sample equal in amount to said quantity of said first sample deposited through steps (A), (B) and (C).

2. A method according to claim 1 of permitting the capillary action of the interstitial structure of said element to withdraw said liquid sample from said tube.

3. A method according to claim 1 which includes the additional step of decreasing the volume of said container as a function of the proximity of said one end of said tube to said chromatographic element, thereby discharging said sample from said tube.

4. A method according to claim 3 wherein said container is a bellows.

5. A method according to claim 1 which includes the steps of:
  positioning said one end of said capillary tube to form a small gap relative to said element, and
  applying said fluid pressure to form a droplet at said one end of said capillary tube sufficient to bridge said gap.

6. A method according to claim 1 wherein said one end of said capillary tube is positioned to contact said chromatographic element.

7. An apparatus for reproducibly depositing predetermined quantities of liquid samples on chromatographic elements comprising in combination;
  a capillary tube,
  a sample receptacle,
  first drive means for raising and lowering one end of said tube with respect to said receptacle and to said element and to transfer said tube between said receptacle and said element, said drive means operable to maintain a predetermined gap between said one end of said tube and said elements and said pressure means forms a droplet on said one end of said tube sufficient to bridge said gap,
  pressure means for applying to the other end of said tube a fluid pressure greater than local ambient pressure, thereby to at least initiate the deposit of a first liquid sample on said element, and
  means for handling a second sample in a predetermined quantity equal in amount to said first sample in the same manner.

8. An apparatus according to claim 7 wherein said chromatographic element has an interstitial structure such that teh capillary attraction of the interstices exceeds that of said tube for said sample, thereby to withdraw said sample from said tube.

9. Apparatus according to claim 7 which also includes control means responsive to said tube being lowered into said receptacle for adjusting the fluid pressure within said capillary tube to control the volume of sample withdrawn by said tube.

10. An apparatus according to claim 7 wherein said pressure means is a closed container having a conduit connected between the other end of said tube and said container, whereby the filling of said tube is controlled by the gas pressure of said container.

11. An apparatus according to claim 10 wherein said container is a resilient bellows.

12. An apparatus according to claim 11 wherein said container is associated with said drive means such that said container is compressed when said tube is lowered toward said element thereby to deposit said liquid sample.

* * * * *